United States Patent [19]

Verbrugge

[11] 4,421,935
[45] Dec. 20, 1983

[54] PROCESS FOR THE PREPARATION OF BICYCLO [2.2.] HEPTENE DERIVATIVES

[75] Inventor: Pieter A. Verbrugge, Amsterdam, Netherlands

[73] Assignee: Shell Oil Company, Houston, Tex.

[21] Appl. No.: 373,832

[22] Filed: May 3, 1982

[51] Int. Cl.$^3$ .............................................. C07C 45/69
[52] U.S. Cl. .................................... 568/343; 568/352; 568/445; 568/591; 568/20
[58] Field of Search .......................... 568/343, 420, 20; 568/352, 445, 591

[56] References Cited

U.S. PATENT DOCUMENTS

| 2,262,002 | 11/1941 | Hopff et al. | 568/349 |
| 3,067,244 | 12/1962 | Robinson et al. | 568/349 |
| 3,341,601 | 9/1967 | Mertzweiller | 568/420 |

FOREIGN PATENT DOCUMENTS

| 29259 | 5/1981 | European Pat. Off. | 568/343 |
| 1045393 | 5/1958 | Fed. Rep. of Germany | 568/343 |

OTHER PUBLICATIONS

Bachner et al., Chem. Abst., vol. 95, #115757F (1981).

Primary Examiner—James H. Reamer
Attorney, Agent, or Firm—Ronald R. Reper

[57] ABSTRACT

Process for the preparation of Diels-Alder type adducts by reacting a compound with formula

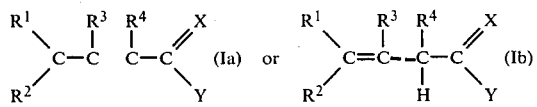

or the corresponding hydrated derivative, wherein $R^1$, $R^2$, and $R^4$ are H or lower alkyl, $R^3$ is lower alkyl, X is O,S, (O—$CR^5R^6R^7$)$_2$ or

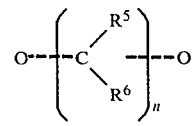

wherein $R^5$, $R^6$ and $R^7$ an H or lower alkyl, n is 2–5 and Y is H, alkyl or alkenyl or Y and $R^2$ together form an alkylene group which may contain one or more substituents, with a cyclopentadiene and/or an oligomer thereof in the presence of an aqueous solution of a strong proton donor having a conjugate with a low nucleophilicity.

10 Claims, No Drawings

PROCESS FOR THE PREPARATION OF BICYCLO [2.2.] HEPTENE DERIVATIVES

BACKGROUND OF THE INVENTION

The present invention relates to a process for the preparation of acyl bicyclo[2.2.1]heptenes and/or derivatives thereof. Acyl bicyclo[2.2.1]heptenes are valuable chemicals per se (e.g. as solvents for dyes and as stabilizers for solutions of dyes in hydrocarbons) and are also useful as intermediates, e.g. for compounds used in modern perfumery.

It is known from Journal f. prakt. Chemie, Band 317, Heft 3, 1975, pages 510–514 that 2-acyl bicyclo[2.2.1-]hept-5-enes can be obtained by reacting cyclopentadiene with methylvinylketone in the presence of (a halogen substituted) acetic acid or aluminum trichloride. No yields are reported therein. Virtually no reaction was observed, however, when cyclopentadiene was brought together with mesityl oxide in the presence of trichloroacetic acid, the fastest Brønsted acid catalyst mentioned in the reference cited hereinbefore. Apparently, the replacement of the hydrogen atoms at the terminal double bond carbon atom almost completely deactivates the reactivity towards Diels-Alder type reactions.

It is also known from Synthesis, Communications, 1979, pages 270–271, that the Diels-Alder adduct of 1,3-cyclohexadiene and acroleine can be obtained in high yield by stirring the reactants during no less than 40 hours at room temperature in the presence of a Nafion-H (tradename) catalyst (resin based). It should be noted, however, that Nafion-H resins, apart from being expensive, are very sensitive to water and can neither be applied successfully in systems wherein water is present as solvent or as reactant nor in systems wherein water is formed during the reaction.

It is thus an object of the present invention to provide a process for the preparation of Diels-Alder type adducts starting from less reactive dienophiles, which process can be carried out using an aqueous catalytic system.

SUMMARY OF THE INVENTION

The present invention therefore relates to a process for the preparation of Diels-Alder type adducts by reacting a compound according to the general formula

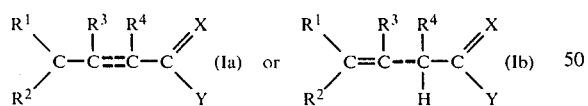

or the corresponding hydrated derivative, wherein $R^1$, $R^2$, and $R^4$, which may be the same or different, each represents a hydrogen atom or a lower alkyl group; $R^3$ represents a lower alkyl group; X represents an oxygen or sulphur atom or a group $(O—CR^5R^6R^7)_2$ or

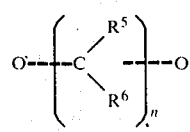

wherein $R^5$, $R^6$ and $R^7$, which may be the same or different, each represents a hydrogen atom or a lower alkyl group; n is an integer of from 2 up to 5 and Y represents a hydrogen atom, an alkyl or alkenyl group or Y and $R^2$ together form an alkylene group which may contain one or more substituents, with a cyclopentadiene and/or an oligomer thereof in the presence of an aqueous solution of a strong proton donor having a conjugate base with a low nucleophilicity.

DESCRIPTION OF THE PREFERRED EMBODIMENTS

Without wishing to be bound to any particular theory, it is thought that the compounds to be reacted with a cyclopentadiene under the reaction conditions according to the present invention should contain an enolizable carbonyl group, while the carbon atom at the beta position, vis a vis the carbonyl group, should be capable of carbenium ion formation (for instance, by protonation or solvolysis).

The present invention relates in particular to a process for the preparation of Diels-Alder type adducts by reacting a compound according to the general formula Ia or Ib or the corresponding hydrated derivative wherein $R^1$, $R^2$, and $R^4$, which may be the same or different, each represents a hydrogen or a methyl group; $R^3$ represents a lower alkyl group; X represents an oxygen atom or a group $(O—CR^5R^6R^7)_2$ or

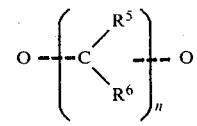

wherein $R^5$, $R^6$ and $R^7$ each represents a hydrogen atom; n is an integer of from 2 to 4, and Y represents a hydrogen atom, an alkyl group of up to three carbon atoms or an alkenyl group of up to 6 carbon atoms, with cyclopentadiene in the presence of an aqueous solution of a strong proton donor having a conjugate base with a low nucleophilicity.

The process according to the present invention is very suitable for the preparation of the Diels-Alder adducts according to the general formula

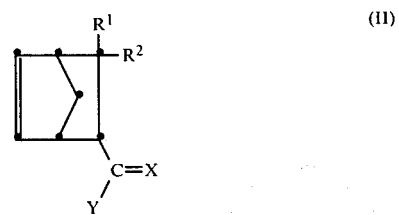

wherein $R^1$, $R^2$, X and Y are as defined hereinbefore, by reacting cyclopentadiene with mesityl oxide and/or diacetone alcohol (general formula Ia wherein $R^1$, $R^2$ and Y represent methyl groups) or derivatives thereof according to formula Ia or Ib in the presence of an aqueous solution of a strong proton donor having a conjugate base with a low nucleophilicity.

It will be appreciated that the bicyclo[2.2.1]heptene derivatives are normally obtained as a mixture of endo- and exo-isomers. The isomers are defined by the position of the —C(=X)Y group in formula II vis a vis the bridging methylene group in the bicyclic structure: in the endo-isomer this group is directed away from and in the exo-isomer it is directed towards the bridging group.

Examples of compounds according to formula Ia and Ib which can be used suitably as starting materials in the process according to the present invention comprise the ketones 4-methyl-3-penten-2-one (mesityl oxide), 4-methyl-4-penten-2-one, 4-methyl-3-hexen-1-one, 2,5,5-trimethyl-1-hexen-4-one, 4,5,5-trimethyl-3-hexen-2-one, 5-methyl-4-hexen-3-one, 2,5,5-trimethyl-4-hexen-3-one, 2-methyl-1-hexen-4-one, 2,5,5-trimethyl-1-hexen-4-one, 2-ethyl-1-penten-4-one, 2-methyl-1-hexen-4-one, 2-ethyl-5,5-dimethyl-1-hexen-4-one and 2,6-dimethyl-2,5-heptadien-3-one (phorone). It will be appreciated that the use of phorone as a starting material allows the formation of a double Diels-Alder adduct.

It is also possible to make use of ketones or aldehydes which have been formed in situ, e.g. by a catalytic aldol condensation reaction from the appropriate precursor(s).

Also, the (a)cyclic ketals corresponding to the ketones mentioned hereinbefore can be used as starting materials in the process according to the present invention. Examples of suitable cyclic ketals comprise the ketals of mesityl oxide or phorone and ethylene glycol or 1,3-dihydroxypropane. It should be noted that the cyclic ketals may also have structures corresponding to formula Ib. In practice, one will often work with mixtures of cyclic ketals (having double bonds as indicated by the formula Ia and Ib) since they will have been prepared that way.

Suitable compounds according to formula Ia or Ib wherein Y represents a hydrogen atom comprise, for instance, 3-methyl crotonic aldehyde and dihydrocitral.

Also, compounds according to formula Ia or Ib wherein the carbon-carbon double bond has been hydrated can be used suitably as starting materials.

Examples of such hydrated, i.e. hydroxy-derivative compounds comprise 4-hydroxy-4-methyl-pentanone-2(diacetone alcohol), 4-hydroxy-4-methyl-hexanone-2, 4-hydroxy-4,5,5-trimethyl hexanone-2, 6-hydroxy-2,6-dimethyl-2-hepten-4-one and 5-hydroxy-4-methyl pentanone-2. Also, mixtures of compounds according to the general formula Ia or Ib and the corresponding hydroxy-derivatives can be used. The compounds according to formula Ia or Ib and/or the corresponding hydroxy-compounds are reacted with cyclopentadiene or an alkyl derivative thereof or with compounds which are capable of producing such cyclopentadienes under the reaction conditions such as the well-known oligomers of cyclopentadiene, e.g. dicyclopentadiene, tricyclopentadiene and tetracyclopentadiene. The molar ratio of the reactants to be employed is not critical and can vary between wide limits. Normally, ratios of compound according to formula Ia (or Ib) to cyclopentadiene of from 5:1 to 1:5 can be suitably applied, preference being given to the use of a slight excess (e.g. up to 50% mol) of the compound according to the formula Ia (or Ib) since this facilitates the working up of the reaction mixture.

It has been found that the process according to the present invention can be carried out using an aqueous acidic catalytic system which comprises a strong proton donor having a conjugate base with a low nucleophilicity. Examples of acids which can be used conveniently are: sulphuric acid, phosphoric acid, perchloric acid, methane sulphonic acid, trihalomethane sulphonic acids and aromatic sulphonic acids such as para toluene sulphonic acid. Preference is given to the use of sulphuric acid and para toluene sulphonic acid.

Normally, the concentration of the acids applied can vary between wide limits, preference being given to the use of acids having a concentration of at least 25%w. Very good results have been obtained using concentrations in the range of from 35%w to 85%w, the optimum being somewhat depending on the particular acid employed. The ratio of acid to reactants can also be varied between wide limits. Ratios of cyclopentadiene to acid in the range of from 100:1 to 2:1 can be applied conveniently, preference being given to ratios between 50:1 and 5:1.

The process according to the present invention can be carried out at relatively low temperatures, e.g. less than about 25° C. It has been found that ambient temperatures or slightly below are adequate to obtain a good conversion and a high selectivity of the product desired. It may even be necessary to cool the reaction to temperatures below 0° C. in order to cope with the exothermicity of process involved.

Sometimes it may be beneficial to apply an inert solvent boiling at a low temperature, e.g. less than about 75° C., such as pentane or hexane or dichloromethane for heat dissipation.

Normally, the process according to the present invention will be carried out at autogeneous pressure, but higher pressures can be used, if desired. The process can be carried out batchwise, semi-continuously or continuously. It is possible to recycle part or all of the catalyst, reactants and/or by-products (such as diacetone alcohol from mesityl oxide) to the reactor in order to obtain a very high conversion of the starting materials.

The reaction mixture can be worked up after the reaction by methods known to the art. The product can be isolated by removal of the starting materials, e.g. by fractional distillation.

The invention will be now illustrated by means of the following Examples. The products were identified using Gas Liquid Chromatography, Mass Spectrometry and Proton Magnetic Resonance Spectroscopy.

EXAMPLE 1

(a) In a reaction vessel were placed mesityl oxide (25 mmol) and 64%w phosphoric acid (1.2 ml). To this mixture was added freshly distilled cyclopentadiene (40 mmol). After the exothermic reaction observed had subsided the reaction mixture was kept for four hours. The conversion amounted to 55%, calculated on the starting material mesityl oxide. 1,1-Dimethyl-2-acetyl bicyclo[2.2.1]heptene was obtained in 47% yield with a selectivity of 85%. Some diacetone alcohol had also been formed.

(b) The experiment was repeated using 1.5 ml phosphoric acid. After one hour 39.6% of mesityl oxide had been converted. 1,1-Dimethyl-2-acetyl bicyclo[2.2.1]heptene had been formed with a selectivity of 78%. Some diacetone alcohol had also been formed.

EXAMPLE 2

(a) The experiment described in Example 1 (a) was repeated, but using 50 mmol of cyclopentadiene and 40%w sulphuric acid (0.8 ml). The reaction mixture was kept for four hours. The conversion of mesityl oxide amounted to 56.7%. 1,1-Dimethyl-1-acetyl bicyclo[2.2.1]heptene had been formed with 64% selectivity. A relatively high amount of diacetone alcohol had been formed as well. When this experiment was repeated in the presence of sufficient sodium sulphate to saturate the initial aqueous sulphuric acid solution, the conversion after four hours amounted to 63.3%. 1,1-Dimethyl-2-acetyl bicyclo[2.2.1]heptene had been formed with 74% selectivity and the amount of diacetone alcohol produced was decreased.

(b) The experiment described in Example 2 (a) was repeated using 35 mmol of cyclopentadiene and 1 ml of sulphuric acid (40%w). After one hour, 48.9% of mesityl oxide had been converted into 1,1-dimethyl-2-acetyl[2.2.1]heptene. The endo/exo isomer ratio of the product amounted to 0.5. When the experiment was carried out using 50 mmol of cyclopentadiene in the presence of 0.8 ml of sulphuric acid, 1,1-dimethyl-2-acetyl bicyclo[2.2.1]heptene had been formed in 64.8% yield after a reaction time of four hours.

EXAMPLE 3

In a reaction vessel were placed mesityl oxide (25 mmol) and 4%w perchloric acid (0.5 ml). To this mixture was added freshly distilled cyclopentadiene (40 mmol). After two hours the reaction mixture was analyzed. 1,1-Dimethyl-2-acetyl bicyclo[2.2.1]heptene had been formed in 82.4% yield.

EXAMPLE 4

The experiment described in Example 2 (b) was repeated using 40 mmol of mesityl oxide and 6.25 mmol methane sulphonic acid. After 50 minutes, the reaction mixture was analyzed. 1,1-Dimethyl-1-acetyl bicyclo[2.2.1]heptene had been produced in 57.4% yield. The endo/exo isomer ratio of the product amounted to 1.7. When the experiment was repeated using 25 mmol of mesityl oxide and 2 mmol methane sulphonic acid, 1,1-dimethyl-1-acetyl bicyclo[2.2.1]heptene had been produced in 76.5% yield after a reaction time of four hours. The endo/exo isomer ratio of the product amounted to 0.25.

EXAMPLE 5

In a reaction vessel were placed mesityl oxide (50 mmol), para toluene sulphonic acid (10.5 mmol) and water (1 ml). To this mixture was added freshly distilled cyclopentadiene (25 mmol). The reaction mixture was kept for four hours at ambient temperature. 1,1-Dimethyl-2-acetyl bicyclo[2.2.1]heptene had been formed in 23% yield.

COMPARATIVE EXAMPLE A

The experiment described in Example 2 (a) was carried out but using 1 ml 1 N hydrochloric acid. After four hours the reaction mixture was analyzed. Only traces of the desired bicyclic compound could be found. When the experiment was carried out using 1 ml of 5 N hydrochloric acid, 1,1-dimethyl-2-acetyl bicyclo[2.2.1-]heptene had only been formed in an amount of 5%.

COMPARATIVE EXAMPLE B

The experiment described in Example 1 (a) was repeated using 1 g of oxalic acid dihydrate instead of phosphoric acid. The contents of the reaction vessel was analyzed after four hours, and no reaction had taken place.

EXAMPLE 6

In a reaction vessel were placed diacetone alcohol (25 mmol) and para toluene sulphonic acid (8.1 mmol). To this mixture was added freshly distilled cyclopentadiene (33 mmol). The reaction mixture was kept at ambient temperature for a period of four hours. 1,1-Dimethyl-2-acetyl bicyclo[2.2.1]heptene had been formed in 56.4% yield. When the reaction was repeated using 40 mmol of cyclopentadiene, 63.6% of product had been formed which showed an endo/exo isomer ratio of 8.3. A yield of 80% was obtained starting with 50 mmol of cyclopentadiene under otherwise similar reaction conditions. When this reaction was carried out at 0° C., the yield of 1,1-dimethyl-2-acetyl bicyclo[2.2.1]heptene amounted to 22%, and the endo/exo isomer ratio was found to be 0.1.

EXAMPLE 7

The experiment described in Example 6 was repeated using diacetone alcohol (25 mmol), cyclopentadiene (50 mmol) together with mesityl oxide (12.5 mmol). After four hours the reaction mixture was worked up. 1,1-Dimethyl-2-acetyl bicyclo[2.2.1]heptene had been formed in 53% yield. The endo/exo isomer ratio amounted to 0.3. When the experiment was repeated at 0° C. (instead of at ambient temperature), 41% of product had been formed under otherwise similar reaction conditions (endo/exo ratio 0.1). When the experiment was repeated at ambient temperature in the presence of pentane (2 ml), the product had been formed in 67% yield.

EXAMPLE 8

In a reaction vessel were placed a mixture of ketals (25 mmol) (produced by reacting mesityl oxide and ethylene glycol in the presence of an acidic catalyst) and 40% sulphuric acid (0.8 ml). To the resulting mixture was added freshly distilled cyclopentadiene (40 mmol). An exothermic reaction occurred, and when it had subsided the reaction contents were kept for four hours at ambient temperature. The conversion amounted to 66%, and the product (the ethylene glycol based ketal of 1,1-dimethyl-2-acetyl bicyclo[2.2.1]heptene) had been formed with a selectivity of 64%.

EXAMPLE 9

The experiment described in Example 2 (a) was repeated using 2,6-dimethyl-2,5-heptadien-3-one (phorone) as the dienophile. When the reaction mixture was analyzed after four hours the presence of the expected bicyclic structures was confirmed by Proton Magnetic Resonance Spectroscopy (olefinic A-B system).

COMPARATIVE EXAMPLE C

In a reaction vessel were placed mesityl oxide (25 mmol) and 40%w sulphuric acid (1 ml). To this mixture was added 2,3-dimethyl butadiene (40 mmol). The resulting mixture was kept for four hours at ambient temperature. Only 21.7% conversion had taken place, and most of the products obtained were oligomers of 2,3-dimethyl butadiene and hydrated compounds. The selectivity to the expected product (1,2,4,4-tetramethyl-5-acetyl cyclohexene) amounted to 50%. When the experiment was repeated using 40%w sulphuric acid saturated with sodium sulphate (1.5 ml) the conversion dropped to 6.9% and the selectivity to the desired product was only 36%.

COMPARATIVE EXAMPLE D

The first experiment described in Comparative Example C was repeated but using the ethylester of beta-methyl crotonic acid instead of 2,3-dimethyl butadiene.

Although the reaction mixture was kept for several hours at ambient temperature, no indication of adduct formation could be found. A similar result was observed when the acid chloride or the alpha-cyanoester were contacted with cyclopentadiene and a strong proton donor having a conjugate base with low nucleophilicity.

I claim:

1. Process for the preparation of Diels-Alder type adducts which comprises reacting at a temperature less than about 25° C. a compound according to the general formula

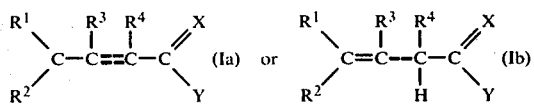

or the corresponding hydrated derivative, wherein $R^1$, $R^2$, and $R^4$, which may be the same or different, each represents a hydrogen atom or a lower alkyl group; $R^3$ represents a lower alkyl group; X represents an oxygen or sulphur atom or a group $(O-CR^5R^6R^7)_2$ or

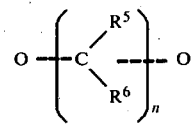

wherein $R^5$, $R^6$ and $R^7$, which may be the same or different, each represents a hydrogen atom or a lower alkyl group; n is an integer of from 2 up to 5 and Y represents a hydrogen atom, an alkyl or alkenyl group or Y and $R^2$ together form an alkylene group which may contain one or more hydrocarbyl substituents, with a cyclopentadiene and/or an oligomer thereof in the presence of an aqueous solution of a strong proton donor having a conjugate base with a low nucleophilicity, wherein the concentration of said donor is at least 25% of the reaction mixture, and wherein said donor is selected from sulphuric acid, phosphoric acid, perchloric acid, methane sulphonic acid, trihalomethane sulphonic acid and an aromatic sulphonic acid.

2. Process according to claim 1, which comprises reacting a compound according to the general formula Ia or Ib or the corresponding derivative wherein $R^1$, $R^2$, and $R^4$, which may be the same or different, each represents a hydrogen atom or a methyl group; $R^3$ represents a lower alkyl group; X represents an oxygen atom or a group $(O-CR^5R^6R^7)_2$ or $$O-\left(C\begin{array}{c}R^5\\R^6\end{array}\right)_n-O$$

wherein $R^5$, $R^6$ and $R^7$ each represents a hydrogen atom; n is an integer of from 2 to 4, and Y represents a hydrogen atom, an alkyl group of up to three carbon atoms or an alkenyl group of up to 6 carbon atoms, with cyclopentadiene.

3. Process according to claim 1, which comprises preparing Diels-Alder adducts according to the general formula

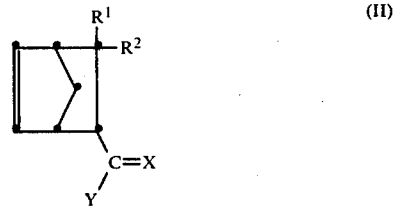

wherein $R^1$, $R^2$, X and Y are as defined hereinbefore, by reacting cyclopentadiene with at least one compound selected from the group consisting of mesityl oxide, diacetone alcohol and their derivatives according to formula Ia or Ib.

4. Process according to any one of claims 1-3, wherein the starting material of the general formula comprises a cyclic or acyclic ketal.

5. Process according to any one of claims 1-3, wherein the starting material of the general formula comprises 3-methyl crotonic aldehyde or dihydrocitral.

6. Process according to any one of claims 1-3, wherein the starting material is a hydrated derivative of a compound according to formula Ia or Ib.

7. Process according to claim 1, wherein the concentration of said donor in the reaction mixture, is from 35% to 85%w.

8. Process according to any one of claims 1-3, wherein the concentration of cyclopentadiene to donor is in the molar ratio range of from 100:1 to 2:1.

9. Process according to any one of claims 1-3, which comprises carrying out the reaction at a temperature less than about 0° C.

10. Process according to any one of claims 1-3, wherein the reaction takes place in the presence of a low boiling solvent which is inert to the reaction.

* * * * *